United States Patent [19]

Raddatz et al.

[11] Patent Number: 5,283,252

[45] Date of Patent: Feb. 1, 1994

[54] THIAZOLYL-SUBSTITUTED QUINOLYLMETHOXYPHENYLACETIC ACID DERIVATIVES

[75] Inventors: Siegfried Raddatz, Cologne; Klaus-Helmut Mohrs; Michael Matzke, both of Wuppertal; Romanis Fruchtmann, Cologne; Armin Hatzelmann, Constance; Reiner Müller-Peddinghaus, Bergisch Gladbach, all of Fed. Rep. of Germany

[73] Assignee: Bayer Aktiengesellschaft, Leverkusen, Fed. Rep. of Germany

[21] Appl. No.: 979,755

[22] Filed: Nov. 23, 1992

[30] Foreign Application Priority Data

Dec. 3, 1991 [DE] Fed. Rep. of Germany ....... 4139751

[51] Int. Cl.$^5$ ................. C07D 417/10; A61K 31/425
[52] U.S. Cl. .................................................... 514/314
[58] Field of Search ................. 546/176, 153; 514/314

[56] References Cited

U.S. PATENT DOCUMENTS

| | | | |
|---|---|---|---|
| 2,708,669 | 5/1955 | Larivé et al. | 546/176 |
| 4,631,287 | 12/1986 | Chakraborty et al. | 514/307 |
| 4,725,619 | 2/1988 | Chakraborty et al. | 514/442 |
| 4,728,668 | 3/1988 | Chakraborty et al. | 514/464 |
| 4,839,369 | 6/1989 | Youssefyeh et al. | 514/314 |
| 4,868,193 | 9/1989 | Lee | 514/314 |
| 4,874,769 | 10/1989 | Youssefyeh et al. | 514/314 |
| 4,963,566 | 10/1990 | Uchida et al. | 546/152 |
| 4,970,215 | 11/1990 | Mohrs et al. | 514/311 |
| 5,089,513 | 2/1992 | Bird et al. | 514/365 |
| 5,091,392 | 2/1992 | Raddatz et al. | 514/311 |

FOREIGN PATENT DOCUMENTS

| | | |
|---|---|---|
| 0339416 | 11/1989 | European Pat. Off. . |
| 0344519 | 12/1989 | European Pat. Off. . |
| 0381375 | 8/1990 | European Pat. Off. . |
| 0399291 | 11/1990 | European Pat. Off. . |

OTHER PUBLICATIONS

J. C. Sheehan, S. L. Ledis, J. Am. Chem. Soc. 95, 875 (1973).
F. E. Frerman et al, Biol. Chem. 258, 7087-7093 (1983).
N. B. Benoton, K. Kluroda, Int. Pept. Prot. Res. 13, 403 (1979).
N. B. Benoton, K. Kluroda, Int. Pept. Prot. Res. 17, 197 (1981).
Borgeat, P. et al, Proc. Nat. Acad. Sci. 76, 2148-2152 (1979).

*Primary Examiner*—David B. Springer
*Attorney, Agent, or Firm*—Sprung Horn Kramer & Woods

[57] ABSTRACT

Thiazolyl-substituted quinolylmethoxyphenylacetic acid derivatives are prepared by reaction of halogenoacetoacetic acid esters with quinolylmethoxyphenylacetic acid thioamides, which are obtainable from corresponding amides with Lawesson's reagent. The substances can be employed in medicaments as inhibitors of enzymatic reactions in the context of arachidonic acid metabolism.

9 Claims, No Drawings

THIAZOLYL-SUBSTITUTED QUINOLYLMETHOXYPHENYLACETIC ACID DERIVATIVES

The invention relates to thiazolyl-substituted quinolylmethoxyphenylacetic acid derivatives, processes for their preparation and their use in medicaments.

Aryl and heteroaryl ethers having a lipoxygenase-inhibiting, anti-inflammatory and anti-allergic action are described in EP 200 101 A2.

Substituted 4-(quinolin-2-yl-methoxy)phenylacetic acid derivatives and α-substituted 4-(quinolin-2-yl-methoxy)phenylacetic acid derivatives moreover are known from EP 344,519 (U.S. Pat. No. 4,970,215) and EP 339,416.

A process for the preparation of lipoxygenase-inhibiting aryl-substituted thiazoles moreover is described in EP 351,194 A2.

The present invention now relates to thiazolyl-substituted quinolylmethoxyphenylacetic acid derivatives of the general formula (I)

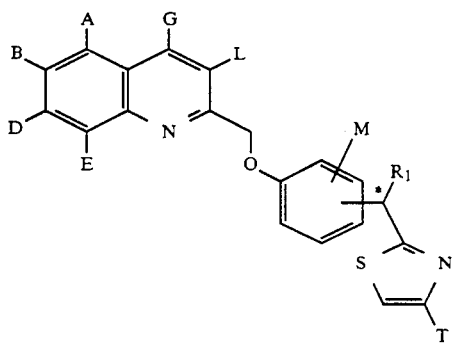

in which

A, B, D, E, G, L and M are identical or different and represent hydrogen, hydroxyl, halogen, cyano, carboxyl, nitro, trifluoromethyl or trifluoromethoxy, or represent straight-chain or branched alkyl or alkoxy having in each case up to 8 carbon atoms, or represent aryl having 6 to 10 carbon atoms, which is optionally substituted by halogen, hydroxyl, nitro or cyano, $R^1$ represents straight-chain or branched alkyl having up to 8 carbon atoms, which is optionally substituted by phenyl or cycloalkyl having 3 to 12 carbon atoms, or represents cycloalkyl having 3 to 12 carbon atoms, which is optionally substituted by straight-chain or branched alkyl having up to 8 carbon atoms, and T represents straight-chain or branched alkyl having up to 6 carbon atoms, or represents the group of the formula

wherein $R^2$ denotes hydrogen or straight-chain or branched alkyl having up to 8 carbon atoms, or denotes benzyl or cycloalkyl having 3 to 12 carbon atoms and $R^3$ denotes a radical of the formula $-OR^4$ or $-NR^5-SO_2-R^6$, wherein $R^4$ denotes hydrogen, straight-chain or branched alkyl having up to 8 carbon atoms or phenyl, $R^5$ denotes hydrogen or straight-chain or branched alkyl having up to 6 carbon atoms or benzyl and $R^6$ denotes aryl having 6 to 10 carbon atoms, which is optionally substituted up to twice in an identical or different manner by halogen, cyano, hydroxyl, nitro, trifluoromethyl, trifluoromethoxy or trifluoromethylthio, or by straight-chain or branched alkyl or alkoxy having in each case up to 8 carbon atoms, or denotes straight-chain or branched alkyl having up to 8 carbon atoms, which is optionally substituted by phenyl, which in turn can be substituted by halogen, cyano, nitro, trifluoromethyl, trifluoromethoxy, trifluoromethylthio or hydroxyl or by straight-chain or branched alkyl or alkoxy having in each case up to 6 carbon atoms, if appropriate in an isomeric form, and salts thereof.

Physiologically acceptable salts are preferred in the context of the present invention. Physiologically acceptable salts of the thiazolyl-substituted quinolylmethoxyphenylacetic acid derivatives can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts in the context of the present invention moreover are salts of monovalent metals, such as alkali metals, and the ammonium salts. The sodium, potassium and ammonium salts are preferred.

The compounds according to the invention exist in stereo-isomeric forms (*), which either behave as image and mirror image (enantiomers), or do not behave as image and mirror image (diastereomers). The invention relates both to the antipodes and to the racemic forms, as well as the diastereomer mixtures. Like the diastereomers, the racemic forms can be separated into the stereoisomerically uniform constituents in a known manner [compare E. L. Eliel, Stereochemistry of Carbon Compounds, McGraw Hill, 1962].

Preferred compounds of the general formula (I) are those in which

A, B, D, E, G, L and M are identical or different and represent hydrogen, hydroxyl, fluorine, chlorine, bromine, carboxyl, nitro, trifluoromethyl or trifluoromethoxy, or represent straight-chain or branched alkyl or alkoxy having in each case up to 6 carbon atoms, or represent phenyl, which is optionally substituted by fluorine, chlorine, bromine, hydroxyl, nitro or cyano, $R^1$ represents straight-chain or branched alkyl having up to 6 carbon atoms, which is optionally substituted by phenyl, cyclopropyl, cyclopentyl, cyclohexyl or cycloheptyl, or represents cyclopropyl, cyclobutyl, cyclopentyl, cyclohexyl, cycloheptyl or cyclooctyl, which are optionally substituted by straight-chain or branched alkyl having up to 6 carbon atoms, and T represents straight-chain or branched alkyl having up to 4 carbon atoms, or represents the group of the formula

wherein
R² denotes hydrogen or straight-chain or branched alkyl having up to 6 carbon atoms, or denotes benzyl, cyclopropyl, cyclobutyl, cyclopentyl, cyclohexyl or cycloheptyl and
R³ denotes a radical of the formula —OR⁴ or —NR⁵—SO₂—R⁶, wherein
R⁴ denotes hydrogen or straight-chain or branched alkyl having up to 6 carbon atoms,
R⁵ denotes hydrogen or straight-chain or branched alkyl having up to 4 carbon atoms and
R⁶ denotes phenyl, which is optionally substituted by fluorine, chlorine, bromine, iodine or cyano or by straight-chain or branched alkyl or alkoxy having in each case up to 6 carbon atoms, or denotes straight-chain or branched alkyl having up to 6 carbon atoms, which is optionally substituted by phenyl, which in turn can be substituted by fluorine, chlorine, bromine or trifluoromethyl or by straight-chain or branched alkyl or alkoxy having in each case up to 4 carbon atoms,
if appropriate in an isomeric form, and salts thereof.

Particularly preferred compounds of the general formula (I) are those in which
A, B, D, E, G, L and M are identical or different and represent hydrogen, hydroxyl, fluorine, chlorine, bromine or straight-chain or branched alkyl having up to 4 carbon atoms,
R¹ represents straight-chain or branched alkyl having up to 6 carbon atoms, which is optionally substituted by phenyl, cyclopropyl, cyclopentyl or cyclohexyl, or represents cyclopropyl, cyclobutyl, cyclopentyl, cyclohexyl, cycloheptyl or cyclooctyl, which are optionally substituted by straight-chain or branched alkyl having up to 4 carbon atoms, and
T represents methyl, or represents the group of the formula

wherein
R² denotes hydrogen or straight-chain or branched alkyl having up to 4 carbon atoms and
R³ denotes a radical of the formula —OR⁴ or —NR⁵—SO₂—R⁶, wherein
R⁴ denotes hydrogen or straight-chain or branched alkyl having up to 4 carbon atoms,
R⁵ denotes hydrogen, methyl or ethyl and
R⁶ denotes phenyl, which is optionally substituted by fluorine, chlorine, bromine, iodine, methoxy or trifluoromethyl, or denotes straight-chain or branched alkyl having up to 4 carbon atoms, which is optionally substituted by phenyl, which in turn can be substituted by fluorine, chlorine, bromine, methyl or methoxy,
if appropriate in an isomeric form, and salts thereof.

Especially preferred compounds of the general formula (I) are those in which A, B, D, E, G, L and M represent hydrogen.

Compounds which are likewise especially preferred are those in which the radical

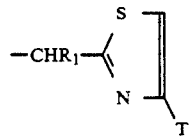

is in the 4-position relative to the quinolylmethoxy radical.

Furthermore, a process has been found for the preparation of the compounds of the general formula (I) according to the invention, characterised in that thioamides of the general formula (II)

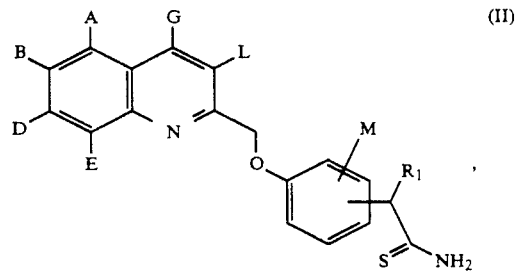

in which A, B, D, E, G, L, M and R¹ have the abovementioned meaning, are reacted with halogenoacetoacetic acid ester derivatives or halogenoketones of the general formula (III)

Cl-CH₂-CO-CH₂-W       (III), in which
W represents hydrogen or C₁-C₆-alkyl, or represents the group —CO—R⁷, wherein R⁷ denotes C₁-C₄-alkoxy, in organic solvents, if appropriate in the presence of water, and in the case of the acids (R³=OH), the esters are hydrolysed by the customary method, and in the case where R² does not represent hydrogen, the reaction is followed by alkylation, and in the case of the sulphonamides (R³=—NH—SO₂R⁶), amidation is carried out in inert solvents, if appropriate in the presence of a base and/or an auxiliary, it being possible for the substituents A, B, D, E, G, L and M to be varied by methods known from the literature at any of the abovementioned stages.

The process according to the invention can be illustrated by way of example by the following equation:

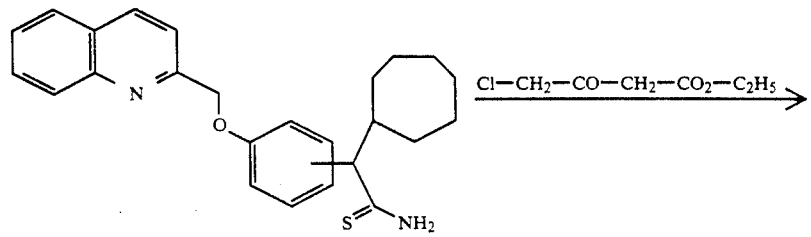

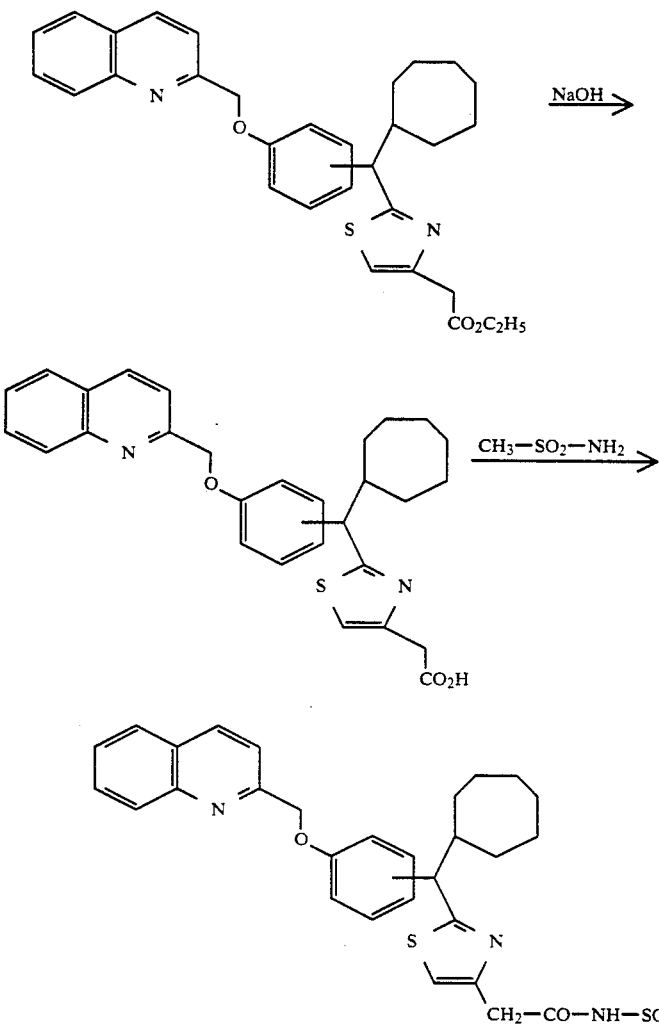

Suitable solvents for the individual reaction steps are in general inert organic solvents which do not change under the reaction conditions. These include, preferably, ethers, such as, for example, dioxane, tetrahydrofuran or diethyl ether, halogenohydrocarbons, such as methylene chloride, chloroform, carbon tetrachloride, 1,2-dichloroethane or trichloroethylene, hydrocarbons, such as benzene, xylene, toluene, hexane, cyclohexane or petroleum fractions, nitromethane, dimethylformamide, acetonitrile, acetone or hexamethylphosphoric acid triamide. It is also possible to employ mixtures of the solvents. Toluene is preferred for the reaction with the compounds of the general formula (II).

The process is in general carried out in a temperature range from 0° C. to 150° C., preferably at 25° C. to 40° C.

The process is in general carried out under normal pressure. However, it is also possible to carry out the process under reduced pressure or under increased pressure (for example in a range from 0.5 to 5 bar).

Suitable solvents for the alkylation are likewise customary organic solvents which do not change under the reaction conditions. These include, preferably, ethers, such as diethyl ether, dioxane, tetrahydrofuran or glycol dimethyl ether, or hydrocarbons, such as benzene, toluene, xylene, hexane, cyclohexane or petroleum fractions, or halogenohydrocarbons, such as methylene chloride, chloroform, carbon tetrachloride, dichloroethylene, trichloroethylene or chlorobenzene, or ethyl acetate, or triethylamine, pyridine, dimethyl sulphoxide, dimethylformamide, hexamethylphosphoric acid triamide, acetonitrile, acetone or nitromethane. It is also possible to use mixtures of the solvents mentioned. Methylene chloride is preferred.

The alkylation is carried out in the abovementioned solvents at temperatures from 0° C. to +150° C., preferably at room temperature up to +100° C., under normal pressure.

The amidation is in general carried out in inert solvents in the presence of a base and a dehydrating agent.

Suitable solvents here are inert organic solvents which do not change under the reaction conditions. These include halogenohydrocarbons, such as methylene chloride, chloroform, carbon tetrachloride, 1,2-dichloroethane, trichloroethane, tetrachloroethane or trichloroethylene, or hydrocarbons, such as benzene, xylene, toluene, hexane, cyclohexane or petroleum fractions, nitromethane, dimethylformamide, acetonitrile or hexamethylphosphoric acid triamide. It is also possible to employ mixtures of the solvents. Methylene chloride is particularly preferred.

Suitable bases for the amidation are the customary basic compounds. These include, preferably, alkali metal hydroxides and alkaline earth metal hydroxides, such as lithium hydroxide, sodium hydroxide, potassium hydroxide or barium hydroxide, alkali metal hydrides, such as sodium hydride, alkali metal carbonates or alkaline earth metal carbonates, such as sodium carbonate or potassium carbonate, or alkali metal alcoholates, such as, for example, sodium methanolate or ethanolate, potassium methanolate or ethanolate or potassium tert-butylate, or organic amines, such as benzyltrimethylammonium hydroxide, tetrabutylammonium hydroxide, pyridine, triethylamine or N-methylpiperidine.

The amidation is in general carried out in a temperature range from 0° C. to 150° C., preferably at 25° C. to 40° C.

The amidation is in general carried out under normal pressure. However, it is also possible to carry out the process under reduced pressure or under increased pressure (for example in a range from 0.5 to 5 bar).

In carrying out the amidation, the base is in general employed in an amount of 1 to 3 mol, preferably 1 to 1.5 mol, per mol of the carboxylic acid.

Suitable dehydrating reagents are carbodiimides, such as, for example, diisopropylcarbodiimide, dicyclohexylcarbodiimide or N-(3-dimethylaminopropyl)-N'-ethylcarbodiimide hydrochloride, or carbonyl compounds, such as carbonyldiimidazole, or 1,2-oxazolium compounds, such as 2-ethyl-5-phenyl-1,2-oxazolium 3-sulphonate, or propanephosphonic anhydride, isobutyl chloroformate, benzotriazolyloxytris-(dimethylamino)phosphonium hexafluorophosphate, phosphonic acid diphenyl ester-amide or methanesulphonyl chloride, if appropriate in the presence of bases, such as triethylamine, N-ethylmorpholine, N-methylpiperidine or dicyclohexylcarbodiimide and N-hydroxysuccinimide [compare J. C. Sheehan, S. L. Ledis, J. Am. Chem. Soc. 95, 875 (1973); F. E. Frerman et al., J. Biol. Chem. 258, 7087–7093 (1983) and N. B. Benoton, K. Kluroda, Int. Pept. Prot. Res. 13, 403 (1979), 17, 187 (1981)].

The hydrolysis of the carboxylic acid esters is carried out by customary methods by treating the esters with customary bases in inert solvents.

Suitable bases for the hydrolysis are the customary inorganic bases. These include, preferably, alkali metal hydroxides or alkaline earth metal hydroxides, such as, for example, sodium hydroxide, potassium hydroxide or barium hydroxide, or alkali metal carbonates, such as sodium carbonate or potassium carbonate, or sodium bicarbonate. Sodium hydroxide or potassium hydroxide is particularly preferably employed.

Suitable solvents for the hydrolysis are water or the organic solvents customary for a hydrolysis. These include, preferably, alcohols, such as methanol, ethanol, propanol, isopropanol or butanol, or ethers, such as tetrahydrofuran or dioxane, or dimethylformamide or dimethylsulphoxide. Alcohols, such as methanol, ethanol, propanol or isopropanol, are particularly preferably used. It is also possible to employ mixtures of the solvents mentioned.

The hydrolysis is in general carried out in a temperature range from 0° C. to +100° C., preferably from +20° C. to +80° C.

The hydrolysis is in general carried out under normal pressure. However, it is also possible to carry out the hydrolysis under reduced pressure or under increased pressure (for example from 0.5 to 5 bar).

In carrying out the hydrolysis, the base is in general employed in an amount of 1 to 3 mol, preferably 1 to 1.5 mol per mol of the ester. Molar amounts of the reactants are particularly preferably used.

Most of the compounds of the general formula (II) are new, and they can be prepared by a process in which amides of the general formula

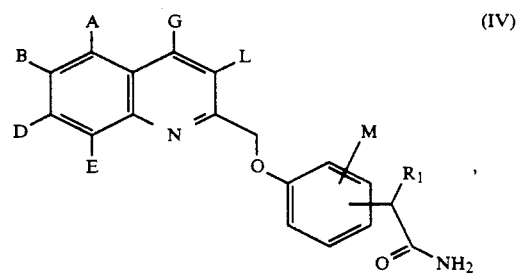

in which A, B, D, E, G, L, M and $R^1$ have the meaning given, are reacted with Lawesson's reagent of the formula (V)

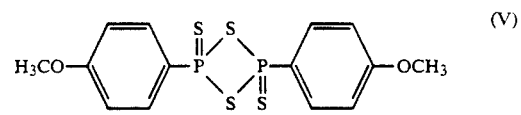

in inert solvents, if appropriate under an inert gas atmosphere.

Some of the compounds of the general formula (IV) are included as intermediate products in the scope of meaning of EP 399,291, but as concrete representative substances are new, and can be prepared, for example, by a process in which compounds of the general formula (VI)

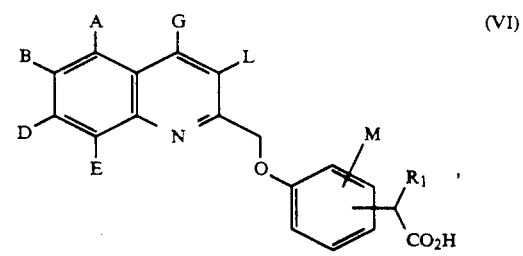

in which A, B, D, E, G, L, M and $R^1$ have the abovementioned meaning, are reacted with carbonyldiimidazole in inert solvents, if appropriate in the presence of one of the abovementioned bases, to give the compounds of the general formula (VII)

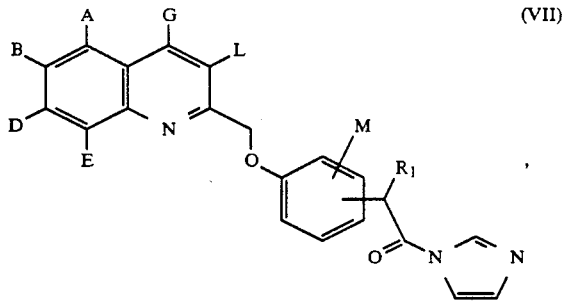

(VII)

in which A, B, D, E, G, L, M and $R^1$ have the abovementioned meaning, and the amides are then prepared in inert solvents in the presence of ammonium chloride and ammonia.

Suitable solvents are the abovementioned solvents. Tetrahydrofuran is preferred for both process steps.

The process is in general carried out under normal pressure. However, it is also possible to carry out the process under reduced pressure or under increased pressure (for example from 0.5 to 5 bar).

The process is in general carried out in a temperature range from 0° C. to +100° C., preferably from +15° C. to +70° C.

The compounds of the general formula (VI) are known [compare U.S. Pat. No. 4,970,715].

The compounds of the general formula (VII) are new and can be prepared by the abovementioned processes.

The compound of the general formula (V) is known [compare MSD 2,2069 B].

The compounds of the general formula (II) are known in some cases, or are new, and in this case can be prepared by the abovementioned method.

Chloroacetoacetic acid derivatives of the general formula (III) are known [compare, for example, Beilstein 3, 663, Part 1, 653].

The pure enantiomers of the compounds of the general formula (I) according to the invention can be prepared, for example, by separating the corresponding enantiomerically pure acids by the customary method and then reacting them further, as described above.

The compounds according to the invention can be employed as active compounds in medicaments. The substances can act as inhibitors of enzymatic reactions in the context of arachidonic acid metabolism, in particular of 5-lipoxygenase.

For example, the compounds of the general formula (I) surprisingly exhibit a high in vitro activity as leukotriene synthesis inhibitors and a potent in vivo action following oral administration.

They are therefore preferably suitable for the treatment and prevention of diseases of the respiratory passages, such as allergies/asthma, bronchitis, emphysema, shock lung, pulmonary hypertension, inflammations/rheumatism and oedemas, thromboses and thromboembolisms, ischaemias (disturbances in peripheral, cardiac and cerebral blood flow), cardiac and cerebral infarctions, disturbances in cardiac rhythm, angina pectoris, arteriosclerosis, in tissue transplant cases, dermatoses, such as psoriasis, inflammatory dermatoses, for example eczema, dermatophyte infections, infections of the skin by bacteria and metastases, and for cytoprotection in the gastrointestinal tract.

The compounds according to the invention can be used either in human medicine or in veterinary medicine.

The pharmacological action data of the substances according to the invention are determined by the following method:

The release of leukotriene $B_4$ ($LTB_4$) on polymorphonuclear human leucocytes (PMN) following addition of the substances and Ca ionophore was determined in vitro by means of reverse phase high performance liquid chromatography by the method of Borgeat, P. et al., Proc. Nat. Acad. Sci. 76, 2148–2152 (1979), as a measure of the 5-lipoxygenase inhibition.

The present invention also includes pharmaceutical formulations which, in addition to inert, non-toxic, pharmaceutically suitable auxiliaries and excipients, comprise one or more compounds of the general formula (I), or which consist of one or more active compounds of the formula (I), and to processes for the preparation of these formulations.

The active compounds of the formula (I) should be present in these formulations in a concentration of 0.1 to 99.5% by weight, preferably 0.5 to 95% by weight of the total mixture.

In addition to the active compounds of the formula (I), the pharmaceutical formulations can also comprise other pharmaceutical active compounds.

The abovementioned pharmaceutical formulations can be prepared in the customary manner by known methods, for example with the auxiliary or excipient substance or substances.

In general, it has proved advantageous to adminster the active compound or compounds of the formula (I) in total amounts of about 0.01 to about 100 mg/kg, preferably in total amounts of about 1 mg/kg to 50 mg/kg of body weight every 24 hours, if appropriate in the form of several individual doses, in order to achieve the desired result.

However, if appropriate, it may be advantageous to deviate from the amounts mentioned, and in particular to do so as a function of the nature and body weight of the subject treated, of the behaviour of the individual towards the medicament, of the nature and severity of the disease, of the nature of the formulation and administration, and of the time or interval at which administration takes place.

STARTING COMPOUNDS

Example I 4-(2-Quinolinylmethoxy)phenyl-cycloheptylacetic acid imidazolide

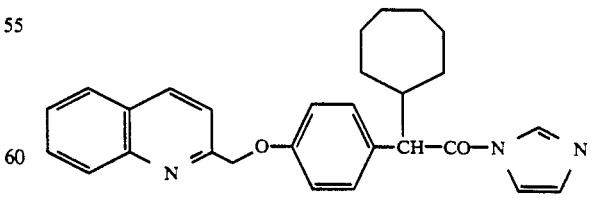

409 g (2.1 mol) of acid and 186.5 g (2.3 mol) of carbonyldiimidazole were stirred in 5 l of tetrahydrofuran at room temperature. After the first evolution of $CO_2$ had subsided, the mixture was stirred at 40° C. until the reaction was complete (high performance liquid chromatography control/thin layer chromatography). The solvent was then distilled off. The residue was dissolved in 2 l of hot isopropanol, and 2 l of water were added. The precipitate was filtered off with suction, washed with ½ l of isopropanol/H₂O (1:1) and then washed again with 1 l of water. It was dried at 50° C. in a circulating air drying cabinet.

Yield: 417 g (90% of theory)
Melting point °C.=146°-148° C.

Example II 4-(2-Quinolinylmethoxy)phenyl-cycloheptyl-acetamide

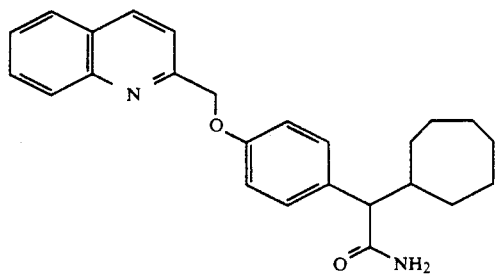

5 g (0.011 mol) of the compound from Example I and a spatula-tip of NH₄Cl were dissolved in 100 ml of tetrahydrofuran, and the solution was heated to about 55° C. A stream of ammonia was passed through the solution at this temperature for 4 hours. The mixture was then allowed to cool and was concentrated to a small volume, and the residue was stirred with methylene chloride.

Yield: 4.1 g (92.8% of theory) of colourless crystals
Melting point: 173° C.

Example III 4-(2-Quinolinylmethoxy)phenyl-cycloheptyl-thioacetamide

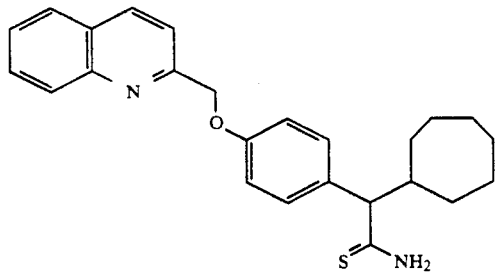

2.0 g (0.0052 mol) of the compound from Example II and 1.3 g (0.0031 mol) of Lawesson's reagent were heated at the boiling point with 15 ml of toluene under an argon atmosphere for 3 hours. The mixture was then separated by column chromatography (silica gel 60, toluene/tetrahydrofuran 100:5). A slightly yellowish product which could be recrystallised from diisopropyl ether was obtained (R_f=0.45).

Yield: 0.9 g (43.2% of theory)
Melting point: 137° C.

PREPARATION EXAMPLES

Example 1

2-[4-(2-Quinolinylmethoxy)phenylcycloheptylmethyl]-4-methyl-thiazole

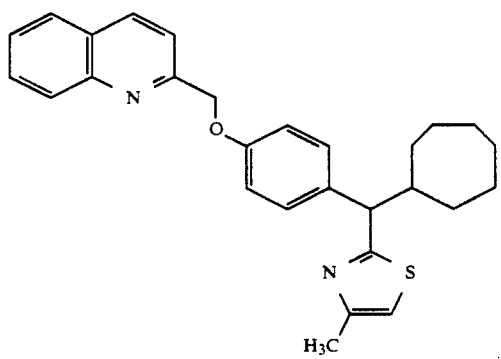

1.5 g (0.0037 mol) of the compound from Example III and 5 ml of chloroacetone are heated with 10 ml of water at 100° C. in an oil bath for 30 minutes. The mixture is then neutralised with sodium bicarbonate solution and extracted with methylene chloride. After the extract has been dried with sodium sulphate, it is concentrated to dryness in vacuo, and the residue is recrystallised in diisopropyl ether.

Yield: 1.3 g (79% of theory)
Colourless crystals, melting point: 119° C.

Example 2

Ethyl 2-[4-(2-quinolinylmethoxy)phenylcycloheptylmethyl]-thiazole-4-acetate

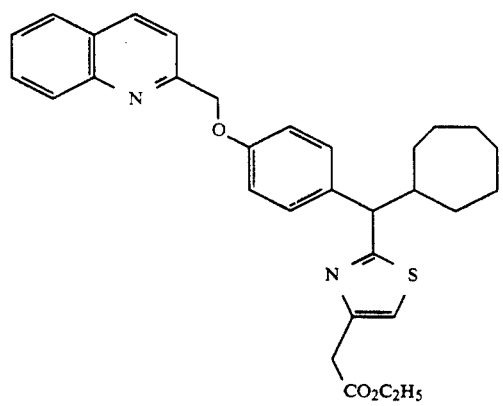

1.5 g (0.0037 mol) of the compound from Example III and 1.5 ml=1.83 g (0.011 mol) of ethyl chloroacetoacetate were heated together with 30 ml of toluene and 10 ml of water at 100° C. for 1 hour. The mixture was neutralised with 10% strength sodium bicarbonate solution, the organic phase was separated off, dried with sodium sulphate and concentrated to a small volume in vacuo, and the residue was separated by column chromatography. A yellow oil was obtained.

Yield: 1.5 g (78.6% of theory)

Example 3

2-[4-(2-Quinolinylmethoxy)-phenylcycloheptylmethyl]-thiazole-4-acetic acid

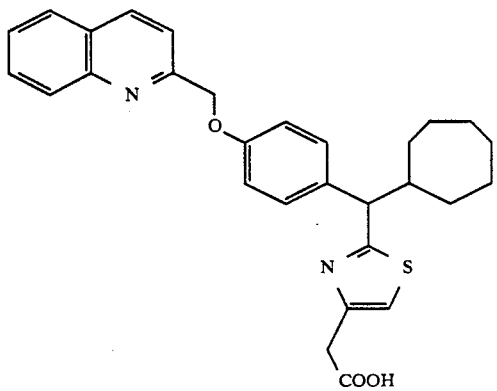

1.4 g (0.00272 mol) of the compound from Example 2 were dissolved in 20 ml of ethanol, 5 ml of 1N sodium hydroxide solution were added, and the mixture was heated at the boiling point for 2 hours. After cooling, 5 ml of 1N hydrochloric acid were added. The colourless precipitate obtained was filtered off and dried. The product is amorphous.

Yield: 1.3 g (98.2% of theory)

Example 4

N-Methylsulphonyl-2-[4-(2-quinolinylmethoxy)phenyl-cycloheptylmethyl]-thiazole-4-acetamide

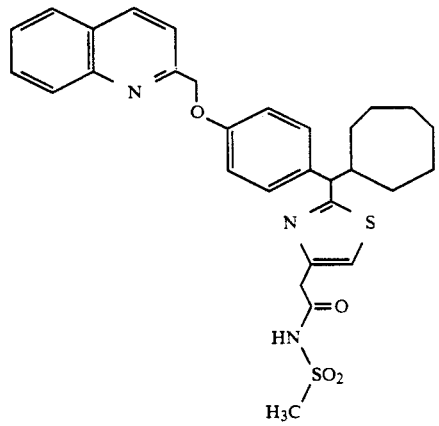

1.5 g (0.0031 mol) of the compound from Example 3, 0.38 g (0.004 mol) of methanesulphonamide, 0.75 g (0.004 mol) of N-dimethylaminopropyl-N-ethyl-carbodiimide hydrochloride and 0.75 g (0.0061 mol) of dimethylaminopyridine (DMAP) were dissolved in 30 ml of dry methylene chloride, and the solution was stirred at room temperature overnight. It was then extracted twice with 30 ml of water, the organic phase was dried with sodium sulphate and concentrated to a small volume in vacuo, and the residue was separated by column chromatography.

$R_f$=0.8 (after evaporation of the solvent: colourless foam)

Yield: 57.6% of theory

We claim:

1. A thiazolyl-substituted quinolylmethoxyphenylacetic acid derivative of the formula

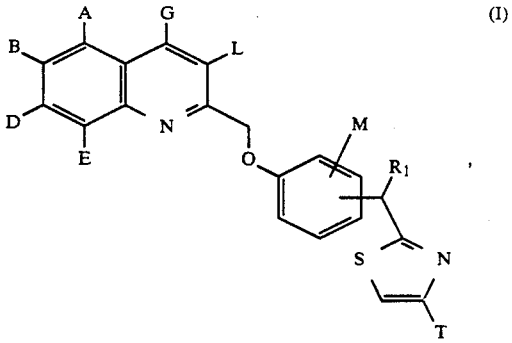

in which

A, B, D, E, G, L and M are identical or different and represent hydrogen, hydroxyl, halogen, cyano, carboxyl, nitro, trifluoromethyl or trifluoromethoxy, or represent straight-chain or branched alkyl or alkoxy having in each case up to 8 carbon atoms, or represent aryl having 6 to 10 carbon atoms, which is optionally substituted by halogen, hydroxyl, nitro or cyano, $R^1$ represents straight-chain or branched alkyl having up to 8 carbon atoms, which is optionally substituted by phenyl or cycloalkyl having 3 to 12 carbon atoms, or represents cycloalkyl having 3 to 12 carbon atoms, which is optionally substituted by straight-chain or branched alkyl having up to 8 carbon atoms, and T represents straight-chain or branched alkyl having up to 6 carbon atoms, or represents the group of the formula

wherein $R^2$ denotes hydrogen or straight-chain or branched alkyl having up to 8 carbon atoms, or denotes benzyl or cycloalkyl having 3 to 12 carbon atoms and $R^3$ denotes a radical of the formula —$OR^4$ or —$NR^5$—$SO_2$—$R^6$, wherein $R^4$ denotes hydrogen, straight-chain or branched alkyl having up to 8 carbon atoms or phenyl, $R^5$ denotes hydrogen or straight-chain or branched alkyl having up to 6 carbon atoms or benzyl and $R^6$ denotes aryl having 6 to 10 carbon atoms, which is optionally substituted up to twice in an identical or different manner by halogen, cyano, hydroxyl, nitro, trifluoromethyl, trifluoromethoxy or trifluoromethylthio, or by straight-chain or branched alkyl or alkoxy having in each case up to 8 carbon atoms, or denotes straight-chain or branched alkyl having up to 8 carbon atoms, which is optionally substituted by phenyl, which in turn can be substituted by halogen, cyano, nitro, trifluoromethyl, trifluoromethoxy, trifluoromethylthio or hydroxyl or by straight-chain or branched alkyl or alkoxy having in each case up to 6 carbon atoms,
or a pharmaceutically acceptable salt thereof.

2. A thiazolyl-substituted quinolylmethoxyphenylacetic acid derivative according to claim 1, wherein
A, B, D, E, G, L and M are identical or different and represent hydrogen, hydroxyl, fluorine, chlorine, bromine, carboxyl, nitro, trifluoromethyl or trifluoromethoxy, or represent straight-chain or branched alkyl or alkoxy having in each case up to 6 carbon atoms, or represent phenyl, which is optionally substituted by fluorine, chlorine, bromine, hydroxyl, nitro or cyano, $R^1$ represents straight-chain or branched alkyl having up to 6 carbon atoms, which is optionally substituted by phenyl, cyclopropyl, cyclopentyl, cyclohexyl or cycloheptyl, or represents cyclopropyl, cyclobutyl, cyclopentyl, cyclohexyl, cycloheptyl or cyclooctyl, which are optionally substituted by straight-chain or branched alkyl having up to 6 carbon atoms, and T represents straight-chain or branched alkyl having up to 4 carbon atoms, or represents the group of the formula

wherein
$R^2$ denotes hydrogen or straight-chain or branched alkyl having up to 6 carbon atoms, or denotes benzyl, cyclopropyl, cyclobutyl, cyclopentyl, cyclohexyl or cycloheptyl and
$R^3$ denotes a radical of the formula $-OR^4$ or $-NR^5-SO_2-R^6$, wherein
  $R^4$ denotes hydrogen or straight-chain or branched alkyl having up to 6 carbon atoms,
  $R^5$ denotes hydrogen or straight-chain or branched alkyl having up to 4 carbon atoms and
  $R^6$ denotes phenyl, which is optionally substituted by fluorine, chlorine, bromine, iodine or cyano or by straight-chain or branched alkyl or alkoxy having in each case up to 6 carbon atoms, or denotes straight-chain or branched alkyl having up to 6 carbon atoms, which is optionally substituted by phenyl, which in turn can be substituted by fluorine, chlorine, bromine or trifluoromethyl or by straight-chain or branched alkyl or alkoxy having in each case up to 4 carbon atoms,
or a pharmaceutically acceptable salt thereof.

3. A thiazolyl-substituted quinolylmethoxyphenylacetic acid derivative according to claim 1, wherein
A, B, D, E, G, L and M are identical or different and represent hydrogen, hydroxyl, fluorine, chlorine, bromine or straight-chain or branched alkyl having up to 4 carbon atoms, $R^1$ represents straight-chain or branched alkyl having up to 6 carbon atoms, which is optionally substituted by phenyl, cyclopropyl, cyclopentyl or cyclohexyl, or represents cyclopropyl, cyclobutyl, cyclopentyl, cyclohexyl, cycloheptyl or cyclooctyl, which are optionally substituted by straight-chain or branched alkyl having up to 4 carbon atoms, and T represents methyl, or represents the group of the formula

wherein
$R^2$ denotes hydrogen or straight-chain or branched alkyl having up to 4 carbon atoms and
$R^3$ denotes a radical of the formula $-OR^4$ or $-NR^5-SO_2-R^6$, wherein
  $R^4$ denotes hydrogen or straight-chain or branched alkyl having up to 4 carbon atoms,
  $R^5$ denotes hydrogen, methyl or ethyl and
  $R^6$ denotes phenyl, which is optionally substituted by fluorine, chlorine, bromine, iodine, methoxy or trifluoromethyl, or denotes straight-chain or branched alkyl having up to 4 carbon atoms, which is optionally substituted by phenyl, which in turn can be substituted by fluorine, chlorine, bromine, methyl or methoxy,
or a pharmaceutically acceptable salt thereof.

4. A thiazolyl-substituted quinolylmethoxyphenylacetic acid derivative according to claim 1, wherein A, B, D, E, G, L and M represent hydrogen.

5. A thiazolyl-substituted quinolylmethoxyphenylacetic acid derivative or salt thereof according to claim 1, wherein the radical of the formula

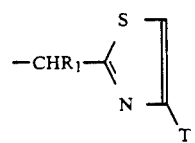

is in the 4-position relative to the quinolylmethoxy radical.

6. A compound according to claim 1, wherein such compound is 2-[4-(2-quinolinylmethoxy)phenylcycloheptylmethyl]thiazole-4-acetic acid of the formula

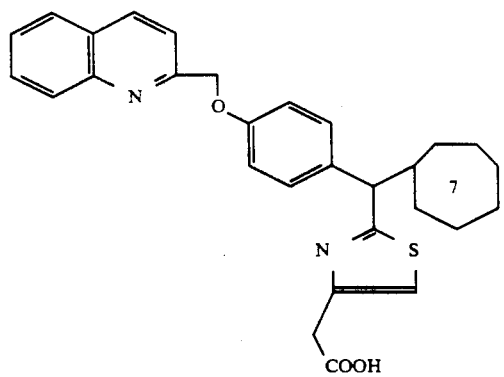

or a pharmacentically acceptable salt thereof.

7. A compound according to claim 1, wherein such compound is N-methylsulphonyl-2-[4-(2-quinolinylmethoxy)phenylcycloheptylmethyl]thiazole-4-acetamide of the formula

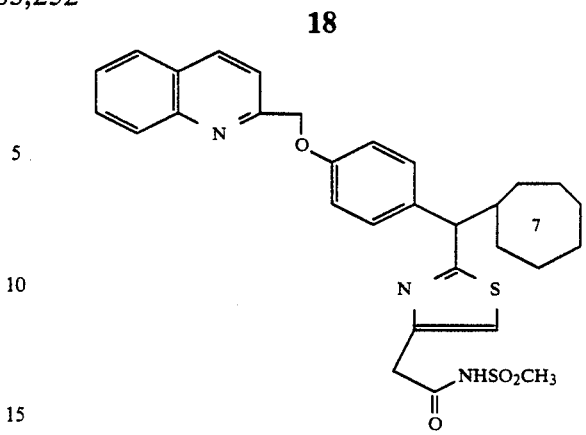

or a salt thereof.

8. A composition for inhibiting the enzymatic reaction in the context of the arachidonic acid metabolism comprising an amount effective therefor of a compound or a salt thereof according to claim 1 and a pharmacologically acceptable diluent.

9. The method of inhibiting enzymatic reactions in the context of the arachidonic acid metabolism in a patient in need thereof which comprises administering such patient an amount effective therefor of a compound or a salt thereof according to claim 1.

* * * * *